US008422377B2

(12) United States Patent
Weiner et al.

(10) Patent No.: US 8,422,377 B2
(45) Date of Patent: *Apr. 16, 2013

(54) REMOTE MONITORING AND DIAGNOSTICS SYSTEM WITH AUTOMATED PROBLEM NOTIFICATION

(75) Inventors: Allison Leigh Weiner, Milwaukee, WI (US); Gopal B. Avinash, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 2177 days.

This patent is subject to a terminal disclaimer.

(21) Appl. No.: 11/015,270

(22) Filed: Dec. 17, 2004

(65) Prior Publication Data

US 2006/0133283 A1   Jun. 22, 2006

(51) Int. Cl.
 *H04J 3/14* (2006.01)
(52) U.S. Cl.
 USPC ...... 370/241; 370/395.42; 709/203; 709/207; 709/219; 705/2; 378/4; 378/117; 600/301; 702/183; 702/187; 702/188
(58) Field of Classification Search .......... 370/241–253, 370/395.42; 709/217, 201, 223, 224, 227, 709/207, 219, 203; 702/122, 188, 34, 57–59, 702/117–121, 182–184, 185; 717/172; 714/4, 714/47; 705/8, 2; 435/6; 378/4, 117; 600/301
 See application file for complete search history.

(56) References Cited

U.S. PATENT DOCUMENTS

| | | | |
|---|---|---|---|
| 4,853,946 A * | 8/1989 | Elliott et al. ...................... | 378/4 |
| 5,067,099 A * | 11/1991 | McCown et al. ............. | 702/183 |
| 5,132,920 A | 7/1992 | Bellows et al. | |
| 5,388,252 A * | 2/1995 | Dreste et al. ..................... | 714/46 |
| 5,852,793 A | 12/1998 | Board et al. | |
| 5,867,714 A * | 2/1999 | Todd et al. ..................... | 717/172 |
| 5,908,392 A * | 6/1999 | Wilson et al. ................. | 600/509 |

(Continued)

FOREIGN PATENT DOCUMENTS

| | | |
|---|---|---|
| EP | 1195681 A2 | 4/2002 |
| WO | WO 01/01301 A2 | 1/2001 |
| WO | WO 03/085469 A2 | 10/2003 |

OTHER PUBLICATIONS

Peter Hobbs, "Remote Telemetry—the Benefits of Trend Analysis and Modern Reporting Mechanisms in Improving Quality of Service and Business Profitability", Intelec 2002, 24th International Telecommunications Energy Conference. Montreal, Quebec, Canada, Sep. 29-Oct. 3, 2002, Intelec. International Telecommunications Energy Conference, New York, NY: IEEE, US, vol. CONF. 24, Sep. 29, 2002, pp. 349-355, XP010614645 ISBN: 0-7803-7512-2.

(Continued)

*Primary Examiner* — Habte Mered
*Assistant Examiner* — Vincelas Louis
(74) *Attorney, Agent, or Firm* — Fletcher Yoder, P.C.

(57) ABSTRACT

A technique is disclosed for servicing complex systems. Upon detection of a serviceable condition, a system snapshot is made and stored. The snapshot may include a range of data then available on the system, particularly hardware configuration data, such as components then installed, peripherals installed, their states, and so forth. The snapshot may include data available prior to the detection of an indicator, at the time of detection and following detection, facilitating evaluation of the condition and potential responses to it.

17 Claims, 6 Drawing Sheets

U.S. PATENT DOCUMENTS

| | | | |
|---|---|---|---|
| 5,923,840 | A | 7/1999 | Desnoyers et al. |
| 5,968,189 | A | 10/1999 | Desnoyers et al. |
| 6,023,507 | A * | 2/2000 | Wookey ................. 709/224 |
| 6,105,149 | A | 8/2000 | Bonissone et al. |
| 6,275,559 | B1 | 8/2001 | Ramani et al. |
| 6,279,125 | B1 * | 8/2001 | Klein ..................... 714/38 |
| 6,324,659 | B1 | 11/2001 | Pierro |
| 6,457,138 | B1 | 9/2002 | Lesser et al. |
| 6,473,659 | B1 | 10/2002 | Shah et al. |
| 6,598,011 | B1 * | 7/2003 | Howards Koritzinsky et al. ..................... 702/185 |
| 6,646,564 | B1 * | 11/2003 | Azieres et al. ........ 340/679 |
| 6,697,962 | B1 * | 2/2004 | McCrory et al. ........ 714/27 |
| 6,708,072 | B2 | 3/2004 | Arima et al. |
| 6,782,345 | B1 * | 8/2004 | Siegel et al. ........... 702/183 |
| 6,892,317 | B1 * | 5/2005 | Sampath et al. ........ 714/4 |
| 6,909,992 | B2 * | 6/2005 | Ashley ................. 702/184 |
| 7,065,564 | B2 | 6/2006 | Machida ............... 709/222 |
| 7,076,520 | B2 * | 7/2006 | Nelson et al. ......... 709/203 |
| 7,079,982 | B2 * | 7/2006 | Ogura et al. ........... 702/185 |
| 7,185,192 | B1 | 2/2007 | Kahn |
| 2001/0053963 | A1 * | 12/2001 | Kim et al. ............ 702/188 |
| 2002/0091850 | A1 * | 7/2002 | Perholtz et al. ....... 709/231 |
| 2002/0109592 | A1 * | 8/2002 | Capano et al. ........ 340/540 |
| 2003/0036939 | A1 * | 2/2003 | Flores et al. ............. 705/8 |
| 2003/0110264 | A1 * | 6/2003 | Whidby et al. ........ 709/227 |
| 2004/0199573 | A1 * | 10/2004 | Schwartz et al. ...... 709/201 |
| 2005/0021311 | A1 * | 1/2005 | Deb et al. .............. 702/188 |
| 2005/0158767 | A1 * | 7/2005 | Haskell et al. ............ 435/6 |
| 2006/0149808 | A1 | 7/2006 | Weiner et al. |
| 2006/0149837 | A1 | 7/2006 | Weiner et al. |
| 2006/0195564 | A1 * | 8/2006 | Accardi et al. ........ 709/223 |
| 2006/0259832 | A1 * | 11/2006 | Kumamoto .............. 714/47 |
| 2008/0041648 | A1 * | 2/2008 | Gardner ................. 180/65.2 |

OTHER PUBLICATIONS

C. S. Batzel et al., "Accumaster Trouble Tracker", AT & T Technology, American Telephone & Telegraph Co. Short Hills, New Jersey, US, vol. 3, No. 2, Jan. 1988, pp. 24-31, XP000118310, ISSN: 0889-8979.

* cited by examiner

REMOTE MONITORING AND DIAGNOSTICS SYSTEM WITH AUTOMATED PROBLEM NOTIFICATION

BACKGROUND

The present invention relates generally to the field of servicing of complex systems, and more particularly to a technique for integrating service data into a knowledge base, permitting improved formulation of service recommendations, prioritization of service recommendations, and creation and processing of system data through a system snapshot, where appropriate.

A range of techniques have been developed for providing remote and local service to complex systems. Where systems are not equipped for remote connectivity, traditional techniques have involved certain self-service procedures. These are typically somewhat limited, and may ultimately require the visit of a qualified service technician who can evaluate malfunctions or anomaly conditions, recommend service, and perform certain service, such as the replacement of parts, reconfiguration, and so forth.

Certain other techniques have been developed for remote servicing. In the medical diagnostics arena, for example, certain systems, particularly more complex and engineered systems (e.g., medical diagnostic imaging equipment) may be equipped for remote connectivity. These systems permit requests for operational service to be sent to a remote service provider, either directly or through a coordinated messaging approach. In certain techniques, the remote provider may automatically process requests, such as to place the request in a service queue, sending notifications back to the originating service requester. Current technology in this field, however, generally relies upon eventual addressing of the service request by a service engineer remotely located from the service system. Based upon the engineer's knowledge and materials available to the engineer, service recommendations may be made, a service technician may be dispatched or other procedures may be followed.

While such techniques are useful for providing service, and particularly remote service, they are not without drawbacks. For example, existing sophisticated servicing procedures often ultimately rely upon the knowledge and experience of the service engineer or other technician who addresses the service concerns. Currently, systems are generally unavailable that can automatically handle service requests by accessing additional information, to harness a wide range of data as it becomes available to the service provider.

Similarly, service request and response prioritization is generally quite reactive. To the extent that any prioritization is carried out in the art, this is generally based upon "first-come/first-served" processing, with little or no re-prioritization based upon relevant factors. Any reprioritization may, for example, simply be based upon an urgency that is conveyed to the service provider by the service requester, such as by telephone, urgent messages, and so forth.

Finally, current techniques do not generally provide a basis for complete evaluation of the service needs. Certain systems allow for capture of error logs, certain system files, and so forth, but generally do not provide a more complete picture in a "snapshot" form. More specifically, current techniques generally do not allow for evaluation of equipment configuration that may be a root cause of a serviceable event.

There is a need, therefore, for further improvements in the field of system servicing, and particularly remote servicing of complex systems.

BRIEF DESCRIPTION

The present invention provides a novel technique for servicing systems designed to respond to such needs. The technique may be applied in a wide range of settings, but is particularly well-suited to remote servicing of complex systems by a remote service provider. Particular fields of interest for application of the techniques might include medical diagnostic equipment, and other systems where reliability and uptime are key. In such systems, proactive remote servicing of many system factors may be the most efficient way to maintain productivity of the system, and the present techniques offer tools for addressing service requests on this basis.

A serviceable event or a condition in a serviced system may be detected by reference to an indicator, such as a performance parameter, operational parameter, error log, and so forth. In response, a service request may be automatically generated. The service request effectively notifies a service provider of the need for servicing a condition, typically an anomaly condition in the system. Based upon a request, the service provider can access an integrated service knowledge base (ISKB) in which service data, prioritization data, service recommendation data, and so forth are stored.

Also in response to service requests, prioritization may be performed by the service provider. Such prioritization may effectively prioritize different responses to the serviceable condition in a single system, but may also include prioritization of service responses between systems, such as when the service provider services a number of different systems. The prioritization may be based upon prioritization scores, and these too may be stored in an ISKB.

The present techniques also provide for capturing a system snapshot upon occurrence of a serviceable condition or event. The system snapshot may include a range of system data, but advantageously includes hardware configuration data which can be correlated with other data from the system and used for evaluation of the serviceable condition or event. In presently contemplated embodiments, the hardware configuration data provides an indication of components installed in the system, as well as peripherals and other hardware which could be the root cause of the serviceable condition, event, or malfunction.

The present techniques also provide for creation and utilization of an ISKB. The ISKB may aggregate, consolidate and correlate data from a wide range of sources, and will generally relate to serviced systems of one or more types and configurations. The ISKB will typically include data identifying systems, data identifying known anomaly conditions or serviceable events, data indicating possible responses and recommendations for servicing the systems, and so forth. The ISKB may also include prioritization information used to prioritize service recommendations both for single systems and for a range of systems and situations. As noted above, the ISKB can be used in automatically responding to and prioritizing responses to service requests.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
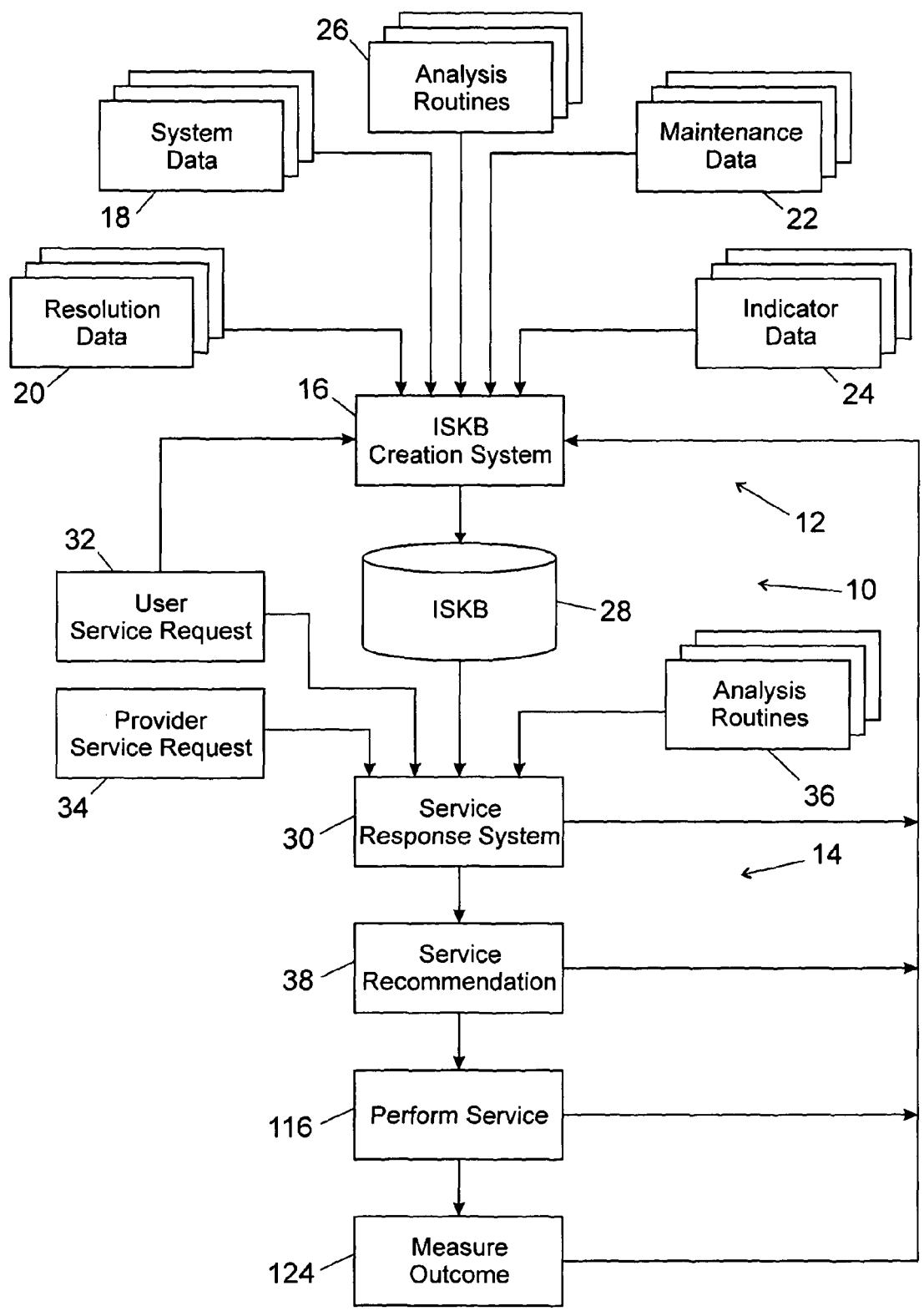
FIG. 1 is a diagrammatical overview of a service system including an ISKB creation system and an ISKB-based servicing system in accordance with aspects of the present technique.

Turning now to the figures, and referring first to FIG. 1, a system 10 is illustrated diagrammatically for servicing complex systems, particularly through remote connectivity between the serviced systems and a service provider. As will be appreciated by those skilled in the art, such complex systems may be of a variety of types, and many such systems may be serviced by the present technique. In an exemplary implementation, for example, serviced systems might include medical diagnostic equipment which may be located in institutions, clinics, hospitals, and the like. Such equipment may be serviced remotely by providing connectivity directly to the system, or through an intermediary, such as a data management system in the institution or by an intermediate data exchange provider. The intermediate data exchange provider may, for example, store service requests, system data, messages, and so forth, and transmit this data to the service provider ultimately responsible for providing actual service to the systems. The service provider may also utilize such an intermediary for responding to the service requests.

It should be noted that, as used herein, the term "service request" and responses to such requests pertain to operational servicing of systems in response to anomaly conditions, malfunctions, and the like. In a general sense, and in certain fields, a "request" for data may be termed a service request. Such requests for data may, in a general sense, include requests for web pages, information, image files, and so forth. However, these requests are not considered as "service requests" in the present context, as they do not address anomaly conditions and events, or malfunctions, or the evaluation or repair of such conditions and events.

In the illustration of FIG. 1, system 10 may be considered as including two somewhat separate but interdependent systems, including an ISKB system 12 and an ISKB-based service system 14. While not all of the features of the present techniques necessarily rely upon a creation or reference to an ISKB, the ISKB is highly useful in providing the service recommendations, prioritization, and other features described herein. The ISKB system 12 includes an ISKB creation system 16 that draws upon a range of sources and data relating to service of the serviced systems. As will be appreciated by those skilled in the art and as described in greater detail below, the ISKB creation system 16 will typically include one or more programmed computers capable of receiving or accessing the needed data and processing the data to establish correlations, links, and relationships between the data used for providing the service described below. The ISKB creation system may include a single computer, where appropriate, which can draw upon databases including the necessary data for the ISKB, or multiple computers with coordinated processing. Not all of the data included in the ISKB is required to be accessed from a pre-established database or reference, however. Certain of the data may be input manually during creation of the ISKB, and may be structured and analyzed during creation of the ISKB as described below.

The ISKB creation system 16 will generally draw upon system data as represented by reference numeral 18 in FIG. 1, as well as problem resolution data 20, relevant maintenance data 22, indicator data 24, and so forth. In general, the system data 18 may identify various types of systems, their known manufacturing information (e.g., manufacturing location, manufacturing date, series numbers, serial numbers, component breakdowns, etc.).

The resolution data 20 may include a range of identified problems and resolutions known for the various systems. For example, the resolution data 20 may identify known "fixes" for problems identified in systems upon manufacture or original delivery, as well as problems and resolutions subsequently identified, such as through service experience, field service visits, and so forth. The resolution data may include hardware configuration resolutions, software configuration resolutions, recommended component and field replaceable unit replacements, and so forth.

Similarly, the maintenance data 22 will typically include information relating to established maintenance procedures that may be carried out or recommended for particular serviced systems. The maintenance data 22 need not relate to individual systems or users, as such information may be drawn later from the systems upon receipt of a service request. Where appropriate, however, such system-specific information may be included in the ISKB.

The indicator data 24 will typically include observable or detectable indicators of possible system malfunction, failure, or impending serviceable conditions or events. Where possible, such indicator data will permit distinguishing various types of serviceable events, as between components, subsystems, and ultimate root causes of the serviceable events and conditions. Again, the indicator data 24 will typically be linked to or correlatable with individual system types, descriptions, definitions, identifications and the like for the various serviced systems.

It should be noted that, as used herein, the terms "indicator" or "indicator data" connote any type of indication of a potentially serviceable condition. The indicators may be parameters (e.g., currents, voltages, various signals), combinations of parameters, and so forth. In certain systems, indicators may be designated, generated or recognized by monitoring or control algorithms, trending algorithms, and the like. Similarly, the serviceable conditions will typically include some type of system malfunction. However, other conditions may be detected and result in processing as described herein, including conditions initiating various tracking, maintenance, and even marketing functions.

In addition to the various types of data drawn upon by the ISKB creation system 16, various analysis routines 26 may be employed. The analysis routines may be incorporated into code defining the ISKB creation system, or may be linked to or drawn upon by the system code as required. By way of example, the routines may permit the identification, analysis, structuring, indexing, classification, and other processes described below. Where data is accessed from unstructured or semi-structured or partially structured data records, for example, the routines may be called upon to structure the record data used for analysis and response to service requests. The analysis routines may also permit correlation of data within and between the various records accessed by the ISKB creation system 16, particularly between the system data, the resolution data, the maintenance data and the indicator data. For example, the ISKB will preferably include correlations between the different types of systems, series or generations of systems, known problems and problem indicators for the systems, known responses to the problems or serviceable conditions, and known or recommended maintenance for the system.

It should be noted that, as described in greater detail below, the ISKB creation system 16 may also establish prioritization for responses to individual known and detectable serviceable events and conditions. For example, particular indicators may lead to a conclusion that a more or less serious condition may have developed or may be developing in a system. Based upon such indicators, and known histories of the issues posed by such problems, prioritization scores may be established for the various indicators, serviceable conditions and events, recommended responses, and so forth. Procedures for establishing such prioritization may be manual, but in a presently contemplated embodiment would be automated or semi-automated by analysis routines accessed by the ISKB creation system 16 during establishment of the ISKB.

Based upon the data accessed by the creation system 16 and upon the routines employed, the ISKB creation system 16 will create the ISKB as indicated generally by reference numeral 28. As will be appreciated by those skilled in the art, the ISKB itself will typically include associated data in one or more databases that would be stored in a permanent storage location or more than one location. In the presently contemplated embodiment, the ISKB is resident on a single storage device, although multiple linked storage devices may, of course, be employed. Moreover, the ISKB is associated with interfaces that permit the stored data, prioritizations, and other features of the ISKB to be accessed for validation, verification, change and reporting. Similarly, interfaces may be provided for submitting information relating to serviceable events or conditions to the ISKB by automatic and/or manual means. Automated submission of and treatment of service requests are described in greater detail below.

As further illustrated in FIG. 1, a service response system 30 forms part of the ISKB-based service system 14. The service response system 30 will typically include one or a plurality of service computers that can draw upon the information in the ISKB and handle service requests from serviceable systems. Where multiple service centers are provided, for example, to service geographically disparate systems, the service response system 30 may include a range of computers linked or linkable to the ISKB 28, and where appropriate linked to each other. As described in greater detail below, the service response system 30 is configured to receive service requests, to draw upon system information and ISKB data, and to respond to or recommend responses to the service request.

In general, service requests may originate from any suitable source. However, in a presently contemplated embodiment, the requests may be generated by a user or a user system as indicated by reference numeral 32, or by a provider as indicated by reference numeral 34. A user service request 32 may, in turn, be automatically generated, as in a presently contemplated embodiment, by a serviceable system upon detection of an indicator of a possible serviceable condition or event, such as a malfunction, failure, or anomaly operation. Provider service request 34 may similarly be generated automatically or manually. Provider service request 34 may, for example, be generated upon identification of a new or previously unknown condition or potential problem in serviced systems, or by field engineers, service engineers, and so forth. Where the provider is able to access or is provided with information relating to system status or performance, moreover, the provider service request 34 may be based upon the provider detecting an indicator of a serviceable event or condition.

Based upon such service requests and upon information in the ISKB, the service response system 30 will typically access analysis routines as indicated at reference numeral 36. These analysis routines permit the service request and any accompanying data, such as a system snapshot as described below, to be processed, structured, analyzed, and so forth. The analysis routines also allow the service request and any accompanying data to be compared to the information in ISKB to establish possible responses to the service request, and prioritization for responses. The prioritization procedures described below may be considered to be carried out through such analysis routines. Based upon the requests, the ISKB data, and the analysis routines, then, one or more service recommendations are made by the service response system as indicated by reference numeral 38. These may take the form of messages, lists and more detailed information displayed at a service workstation, reports generated at the service provider, notifications sent to serviced systems, and so forth. Such service recommendations may also include scheduling and dispatching of parts, technicians, field service engineers, ordering of parts, shipment of parts, or any of a variety of conventional service responses. Where appropriate, service recommendations may also include actual service that can be performed at or remote from the serviced systems, such as by sending a service packet or software to the serviced system. Such packets may be used, for example, to reconfigure, reset or otherwise manipulate the software, firmware, or even hardware installed and operable on the service system.

Following the recommendation, some type of service will typically be performed, as indicated at reference numeral 116 in FIG. 1, and as described below. Based on the service performed, the service and recommendation may be evaluated, such as by measuring the outcome in an appropriate manner (depending upon the nature of the system, the condition and the type of service rendered), as indicated at reference numeral 124, and as also discussed below. It should be noted that certain of the functions summarized in FIG. 1 may result in updating or other correction or supplementation of the ISKB, as indicated by the arrows returning to the ISKB in FIG. 1. This updating function provides for continuous reinforcement, correction and improvement of the service information contained in the ISKB.

Figure 2:
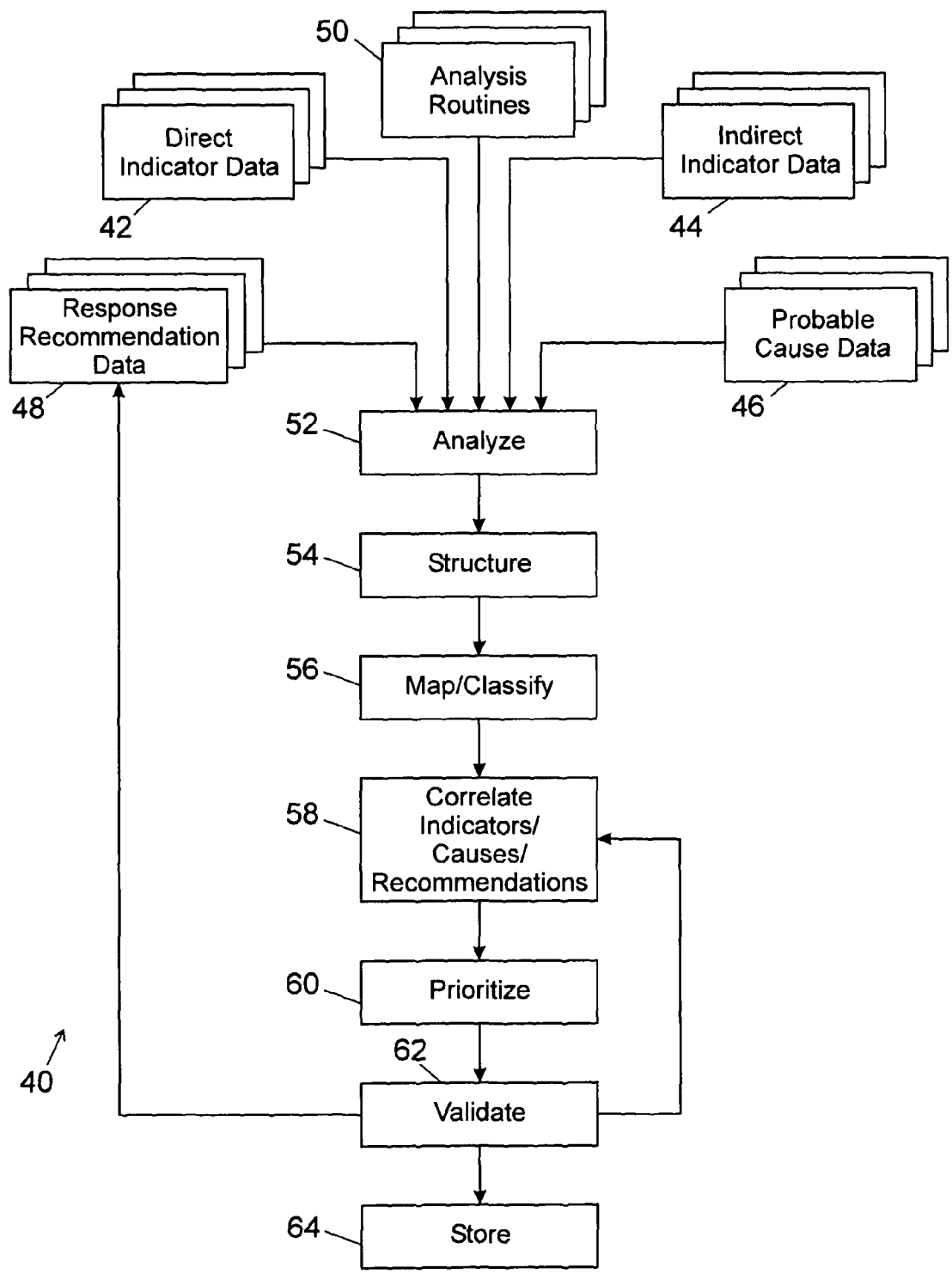
FIG. 2 is a flow chart illustrating exemplary logic in creation of the ISKB.

FIG. 2 represents an exemplary process for creation of the ISKB. The exemplary logic, designated generally by reference numeral 40, will be broken down into a series of steps for receiving and processing the types of data described above. As noted with regard to FIG. 1, the ISKB creation system will typically draw upon system data, problem resolution data, maintenance data and indicator data. As shown in FIG. 2, the indicator data and the resolution data may be further broken down into various specific types of information that may be acquired from known databases, by expert input, by analysis of maintenance records, and so forth. More specifically, as shown in FIG. 2, direct indicator data 42 may be provided, in addition to indirect indicator data 44. Direct indicator data may include, for example, such information as voltages, currents, indicator light or alarm activation, and so forth that are directly indicative of potential serviceable conditions, failures, malfunctions, or developing conditions that may require service. Indirect indicator data 44 may include parameter information that is not directly correlated to a specific type of failure, but for which, typically in combination with other information, indications of anomaly conditions, and their locations and causes can be derived. As will be appreciated by those skilled in the art, many different types of indicators may be identified depending upon the nature and operation of the serviced systems. In general, the indicators permit identification and localization of causes of serviceable conditions and events, while avoiding excessive redundancy that could tax the service response system resources unnecessarily.

In addition to the indicator data, probable cause data 46 may be accessed, where available. Such probable cause data 46 may, in practical applications, be inherently linked to the direct indicator data and indirect indicator data, providing in combination with such data an indication of a potential malfunction both in software and hardware. Where appropriate, the probable cause data may be quite specific in terms of the location and root cause of a malfunction, or may be limited to a particular program, a routine within a program, a field replaceable unit, a sub-assembly, and so forth. As will be appreciated by those skilled in the art, the degree of localization of the ultimate root cause of the malfunction may require further and additional indicators. The economic servicing of the systems may imply the degree of localization of the root cause desired for servicing. That is, a practical service recommendation may include replacement of several components as a field replaceable unit, or reloading or reconfiguring of a block of software, for example, even though the ultimate root cause could theoretically be determined through more investment in sensors, and data collection and analysis.

Response recommendation data 48 is also considered, where available. In a typical ISKB, for example, known problems and "fixes" will be available for populating the ISKB, and additional recommendations may become available over time. These may be linked to specific direct or indirect indicators, and, where possible, to probable root causes of malfunction.

As discussed above, various analysis routines, summarized by reference numeral 50, may be drawn upon for the processing of the accessed data. The analysis routines may permit the processing summarized in FIG. 2 as well as other processing, where appropriate.

As summarized in FIG. 2, the processing begins with analysis of the accessed data, as indicated at reference numeral 52. Such analysis will typically include identification of associations between the accessed data and individual systems or system types. In most complex systems, many different parameters may be monitored and their values or ranges may be stored. The analysis may also include determination of the relevancy of the accessed or available data, such as to determine which, of many different monitored parameter values and ranges available, are of particular interest as indicators of possible malfunction, and which may be less relevant and not retained for addressing a service requests. Where desired, the accessed data may be structured to facilitate its later access, comparison, and association with other data stored in the ISKB, as indicated at step 54. At step 56, the data is mapped and classified, for example, to associate the data with individual systems and system types, individual indicators, groups of indicators, possible root causes and problems, and responses and service recommendations. Similarly, as indicated at step 58, correlations are made between the indicators, causes and recommendations. These correlations will typically be made through a relational database, forming a data structure that will make up the ISKB.

As indicated at step 60 in FIG. 2, and as discussed in greater detail below, the responses and recommendations may be prioritized and prioritizations stored as prioritization scores within the ISKB. Such prioritization may be based upon the severity of root causes of malfunction, the ultimate cost of the malfunction or the repair, the downtime consequent from the malfunction, and so forth. Where several possible root causes and recommendations exist, therefore, such prioritization scores will establish a hierarchy among the recommendations, which would be acted upon by the systems automatically, or with the intervention of service personnel in a particular order, based upon prioritization.

As indicated at step 62 in FIG. 2, a validation procedure is generally in order to verify that the indicators, root cause indications, and recommendations are correct for the service systems. The validation procedure may be performed, for example, by systems experts. Validation may also include validation of the prioritization of the service responses and recommendations. As indicated by the arrow leading from block 62 in FIG. 2, this validation may result in changes in any one of the foregoing steps used to generate the ISKB. Such changes may include, for example, addition or elimination of parameter indicators, addition, elimination or changes in recommendations and responses, and changes in prioritization scores. At step 64, ultimately, the ISKB is stored for use in addressing service concerns.

Figure 3:
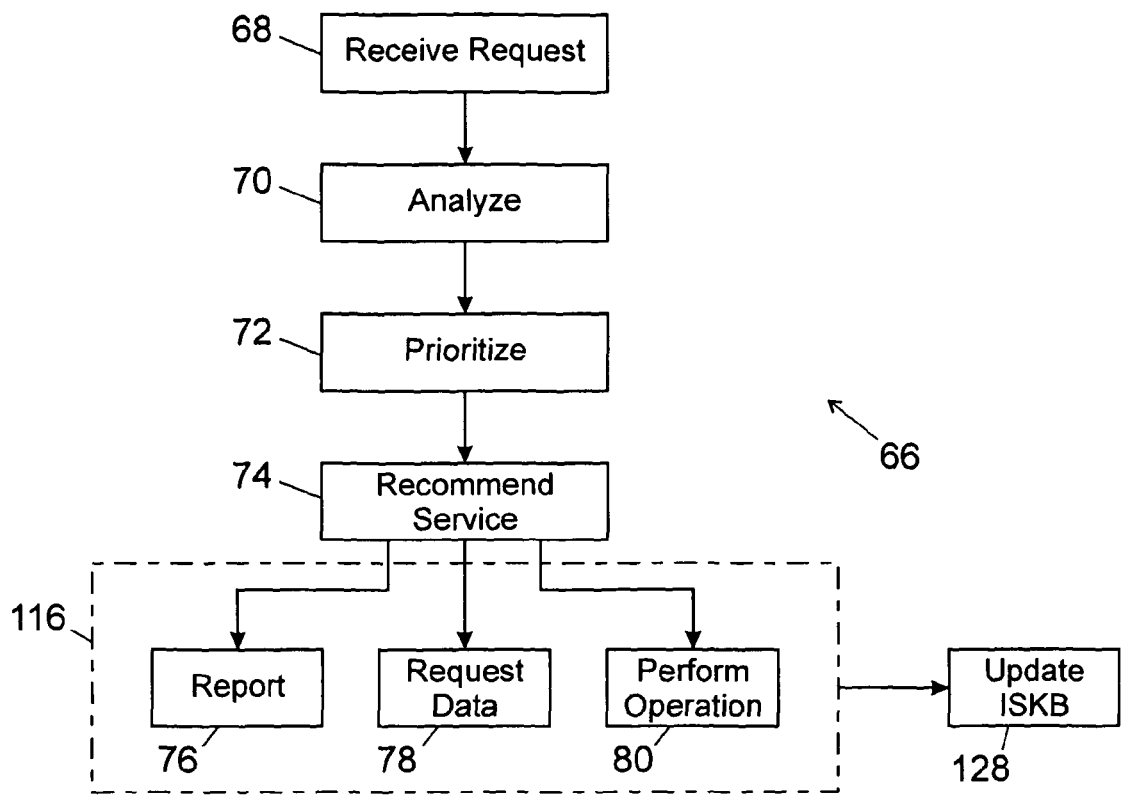
FIG. 3 is a flow chart illustrating exemplary logic in processing service requests.

FIG. 3 illustrates exemplary logic for processing a service request in accordance with aspects of the present technique. The processing logic, designated generally by reference numeral 66, begins with receiving the service request at step 68. The service request will typically be sent in electronic form, such as via an electronic message or the like. The service request may include information such as the system identification, and relevant information on the problem that may be experienced in the system. Moreover, in a presently contemplated embodiment, the service request may include a number of additional components and supporting information, such as a name or designation of the request, the origin of the request, a request frequency designation (e.g., the number of times a similar request has been made), a customer identification, a user identification, a field service technician contact, and so forth. In addition to this basic information, the request may include actual log data and file data that may aid in identifying the serviceable condition or event, and the root cause of the malfunction, and in recommending a service response. Such information may include, for example, log files, image files, audio files, video files, text files, and files otherwise indicating monitored parameters that could serve as indicators useful in addressing the service request.

In accordance with certain aspects of the present technique, the service request may also include configuration data. In presently contemplated embodiment, such data may identify the affected equipment, and any available service history of the system or the particular affected equipment. The configuration data may include software configuration data and hardware configuration data as well. The hardware configuration data is particularly useful in identifying root causes of problems, and in ruling out root causes where hardware or components are not installed or are not enabled. The hardware and software configuration information may be captured in a "snapshot" as described below, and stored in a log file at the system or a remote from the system. Inclusion of this information and service request further facilitates determining a proper response to the service request, as well as the prioritization of responses where several responses are possible. As noted above, the information may also serve to establish priorities at a service provider between service to be made for different systems.

The process of FIG. 3 continues with analysis of the service request as indicated at reference numeral 70. Such analysis will include parsing or structuring of the service request information. At step 72 the service request may be prioritized. As discussed in greater detail below, such prioritization may be based upon a prioritization score stored in the ISKB, or upon factors considered other than in the ISKB, including service contract-based, and other factors.

At step 74, one or more service responses are recommended. Several different types of service responses are presently contemplated. These may be grouped, generally, as indicated by reference numeral 116. For example, as indicated at reference numeral 76, the service responses may include a simple report of the incident to the system personnel, as well as to service providers, field engineers, and so forth. In particular, for certain systems that are is capable of automatically generating a service request, the system overseer, management, owner, or other responsible person may not even be aware of the incident or of the need for service. The report generated at step 76 provides such information. Additionally, the report may provide useful information for dispatching field engineers, notifying the technicians of the occurrence of the service request, and so forth.

In addition, one response might include requesting additional data as indicated at reference numeral 78. Such additional data may result from the service response system identifying that insufficient data is available or has been submitted to permit a satisfactory recommendation to be made, or to differentiate between possible root causes or recommendations. Such additional data may be requested automatically or through user intervention, or by a service technician or other service personnel.

Finally, as indicated at reference numeral 80, specific operations may be performed. These may include the relatively conventional dispatch of a service technician, but may also include highly automated responses. For example, via remote connections and links, where appropriate, certain settings on the serviced system may be altered automatically, such as by transmission of a service packet to the system. Similarly, configuration data may be sent to the system for reconfiguring or resetting (e.g., recalibrating) certain components. Appropriate responses may also include placing certain parts or components on order, or even shipping certain parts or components for possible replacement in the system.

Based upon any one of such service responses, the ISKB may be updated for improvement, as indicated by reference numeral 128, and as discussed in greater detail below.

Figure 4:
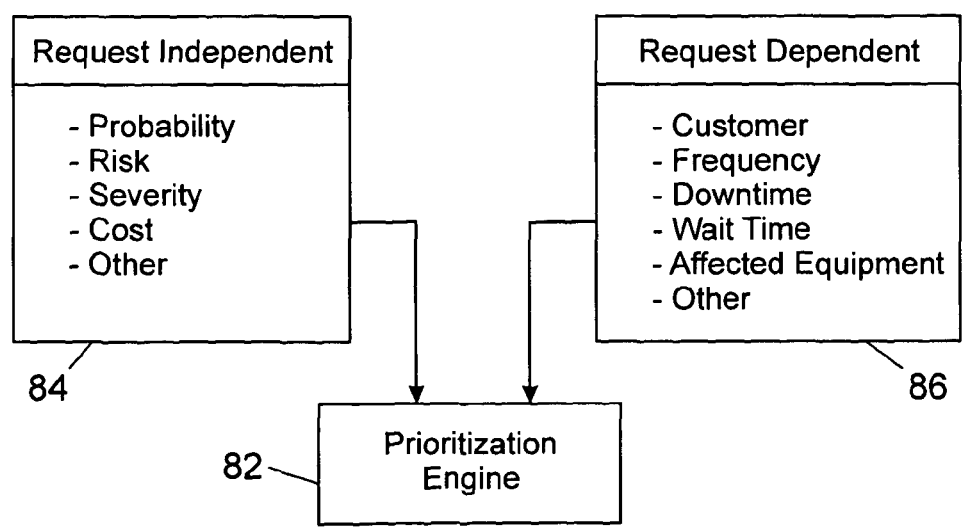
FIG. 4 is a diagrammatical representation of certain types of factors that may be considered in establishing prioritization between service requests and recommendations or responses that may be made to such requests.

The service requests, recommendations, and service actions may be prioritized in accordance with aspects of the present technique, including by the storing of specific prioritization scores for root causes, indicators, suggested responses, and the like. In a presently contemplated embodiment, these prioritization scores are generated as the ISKB is established. As part of the analysis routines implemented by the ISKB creation system, a prioritization engine 82 as illustrated in FIG. 4 may be called upon. The prioritization engine 82 may essentially consist of software implemented by the computer or computers establishing the ISKB, based upon prioritization logic. Such logic will typically vary based upon the nature of the system, the role of the system, and so forth. The prioritization logic may be adapted and especially designed for the system type. The designers of a particular ISKB will typically set the logic, and its coding is considered to be within the purview of capable programmers skilled in the art and does not require undue experimentation.

The prioritization engine and logic may call upon any range of factors for establishing the priority between indicators, root causes and possible responses to service requests. In the embodiment illustrated in FIG. 4, certain of these factors may be considered to be request-independent as indicated at reference numeral 84, while others are considered to be request-dependent as indicated by reference numeral 86. Request-independent factors may include such factors as a probability of failure or downtime, as risk involved with the possible failure (e.g., in terms of downtime, risk to machinery and the environment, etc.), the possible severity of the problem or failure, a cost associated with the problem, failure or downtime, and any other factors. These factors are grouped as request-independent because the do not relate necessarily to the request itself, but are more dependent upon the system and consequences flowing from occurrence of the serviceable event in the system. Request-dependent factors might include such factors as the customer making the request, the frequency with which the request or similar requests have been made, downtime that is being experienced or could be experienced by the customer, wait time that has been experienced or could be experienced by the customer in having the service request responded to, and the affected equipment or other factors. Such factors are more related to the request itself or the source or nature of the request. Based upon such factors, a prioritization score may be assigned to the various known indicators, root causes and responses.

Figure 5:
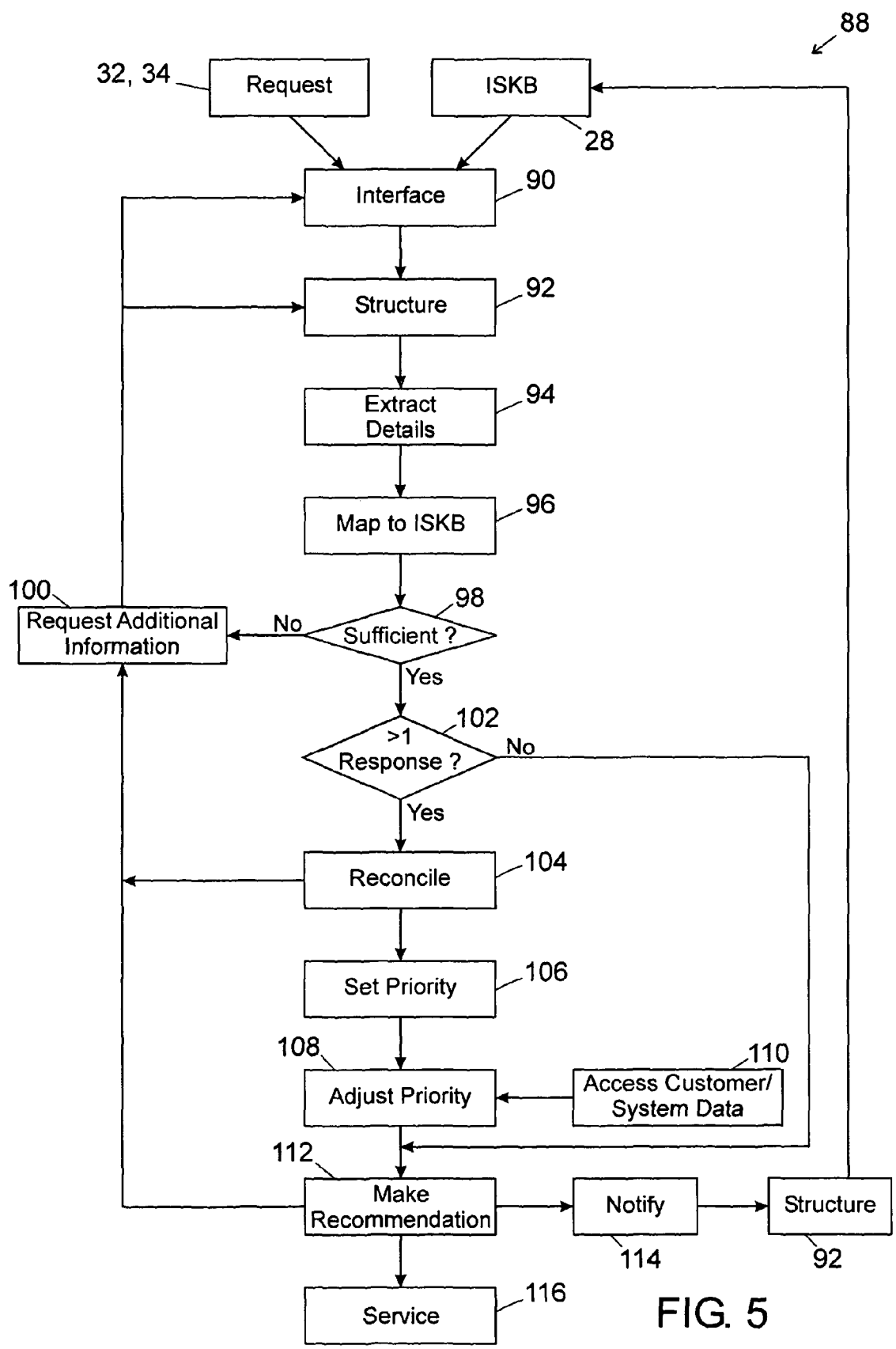
FIG. 5 is a flow chart illustrating processing and prioritization of service requests and recommendations.

FIG. 5 illustrates in somewhat greater detail exemplary logic for prioritizing received service requests. The logic, designated generally by the reference numeral 88, begins with the request itself, 32, 34, and the ISKB 28, which are accessed by an interface 90. As indicated above, the interface will typically be equipped to receive requests automatically, such as by electronic transmission, as well as to access the ISKB either locally or via a remote connection. The request and information from the ISKB may be structured as indicated at step 92. As noted above, the ISKB will typically be pre-structured to facilitate reference to the data it contains. The request, moreover, may also be structured, but may include unstructured or partially structured data which is structured at step 92 to permit evaluation of the service request and its comparison to information in the ISKB.

At step 94, the details of the service request are extracted. These details may include all of the contents described above that may be contained in the service request, including the system identification, identification of the serviceable event or condition, location information, service history information, log files, hardware configurations, and so forth. At step 96, this information is mapped onto the ISKB. This mapping may entail simple comparison of individual fields or data structures, or may include more detailed logic. This logic may be based upon, for example, evaluating specific indicators and correlating such indicators with potential root causes and service recommendations. At step 98 the system may evaluate whether sufficient information was received in the service request. If insufficient information was received, additional information may be requested as indicated at step 100. Such additional information may include, for example, the hardware configuration information described above, error files, log files, or any parameter data which may serve as an indicator of the nature of a serviceable condition or event and a possible root cause and recommended solution.

Where more than one possible response is available, this may be evaluated at step 102. If more than one response is not available, processing can continue and the single available recommendation can be made as discussed below. However, where more than one response is available, these may be reconciled at step 104. The reconciliation of available responses may include elimination of certain responses, inclusion of certain responses, and so forth. Such reconciliation may be performed automatically based upon rules contained in the ISKB or implemented by the service response system. Such reconciliation may also be performed based upon input from service technicians, experts, and the like.

At step 106 a priority may be set between or among possible responses. As noted above, this priority may exist between possible responses to a single serviceable condition, or possible serviceable conditions within a single system, or may be between systems. That is, where a service provider offers service to a number of different systems or customers, certain serviceable conditions may take precedent over others, such that the priority between and among the service request and the possible responses may require that certain requests be addressed on a higher urgency basis. The priority set at step 106 may, therefore, be set relatively objectively based upon the prioritization scores stored within the ISKB or derived during processing. At step 108 these priorities may be adjusted. Adjustments to the priorities may be made manually or based upon automated rules. By way of example, the priories may be adjusted based upon customer identification, system identification, or more broadly based upon service contracts. By way of example, where several levels of service contracts are offered, the service provider may grant higher priority to certain types of premium service contracts, with a normal level of priority being allocated for other service contracts. Access to such information may be made for the adjustment process, as indicated at step 100 in FIG. 5.

Based upon the prioritization, or if a single recommendation is to be made, the recommendations are output as indicated at step 112. As noted above, the recommendations may include any range of possible responses to the service request. In general, however, the system or system owner will be notified as indicated at step 114. This notification may also be made to the service provider, responsible personnel at a customer and service provider, field engineers and technicians, and so forth. Finally, at step 116, some type of service activity will generally be in order. As also noted above, this service may include an actual field visit to or contact with the system, or an automated "fix" to address the unserviceable condition. Other responses and service could follow any conventional type of response, including regularly or specially scheduled servicing, and so forth. Also, the notification 114 may be structured, as indicated at block 92 adjacent to block 114 in FIG. 5, to facilitate updating and improvement of the data in the ISKB.

Figure 6:
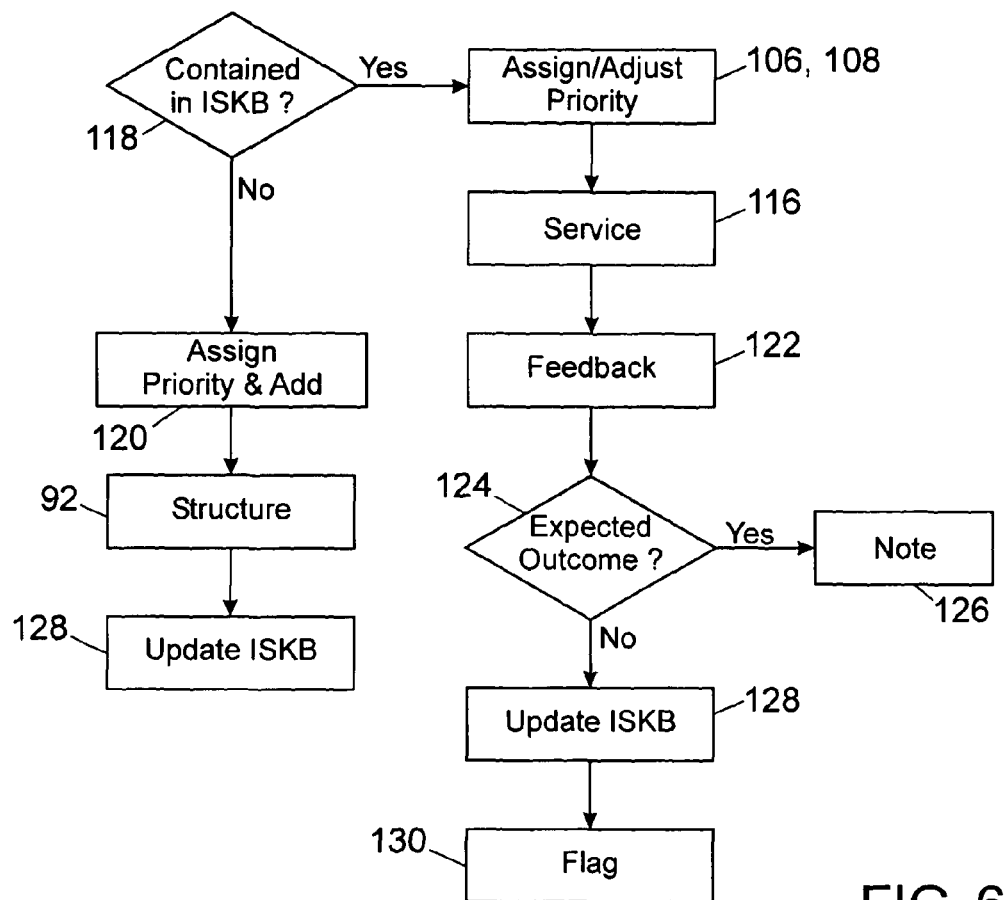
FIG. 6 is a diagrammatical representation of certain logic useful in updating an ISKB based upon service provided.

FIG. 6 represents exemplary logic for updating the ISKB based upon actual servicing and feedback. The logic of FIG. 6 may begin with determination of whether a correlatable serviceable event or condition exists in the ISKB, as denoted by reference numeral 118. As noted above, the ISKB may be based upon existing information and knowledge of serviced systems. However, it is possible and even likely that new serviceable conditions will be recognized and indicators and the responses will be proposed and made for addressing service requests based upon newly recognized conditions. Where the condition or event is not contained in the ISKB, these may be assigned a priority, where the ISKB includes prioritization scores, and the information may be added to the ISKB for addressing future requests of a similar nature, as indicated by reference numeral 120. As before, where such data requires structuring to facilitate its inclusion in the ISKB, this is performed at step 92, followed by updating of the ISKB at step 128.

Where the condition or event is already contained in the ISKB, the service request or response may be assigned a priority and the priority adjusted as indicated above and noted at steps 106, 108 in FIG. 6. Also as noted above, based upon these recommendations, service is ultimately provided as indicated at step 116 in FIG. 6.

Based upon this provided service, feedback may be obtained as indicated at step 122, such as from the system itself, a customer or responsible party, or the field engineer or technician. To provide the maximum utility, the feedback is evaluated to determine whether the outcome of the service was as would have been expected based upon the information in the ISKB, as indicated at step 124. If the feedback is positive (i.e., service had expected outcome), a note of such may be made in the ISKB, as indicated at reference numeral 126. Such positive feedback may serve to reinforce the information in the ISKB, and even increase the prioritization score for such responses. If the expected outcome was not obtained, on the other hand, the ISKB may be updated as indicated at step 128. Such updating may, conversely, result in lowering a prioritization score for the recommendation actually implemented. In general, at step 130, some type of notification or flag may be set indicating to manager of the ISKB that the update has been made or should be made.

Figure 7:
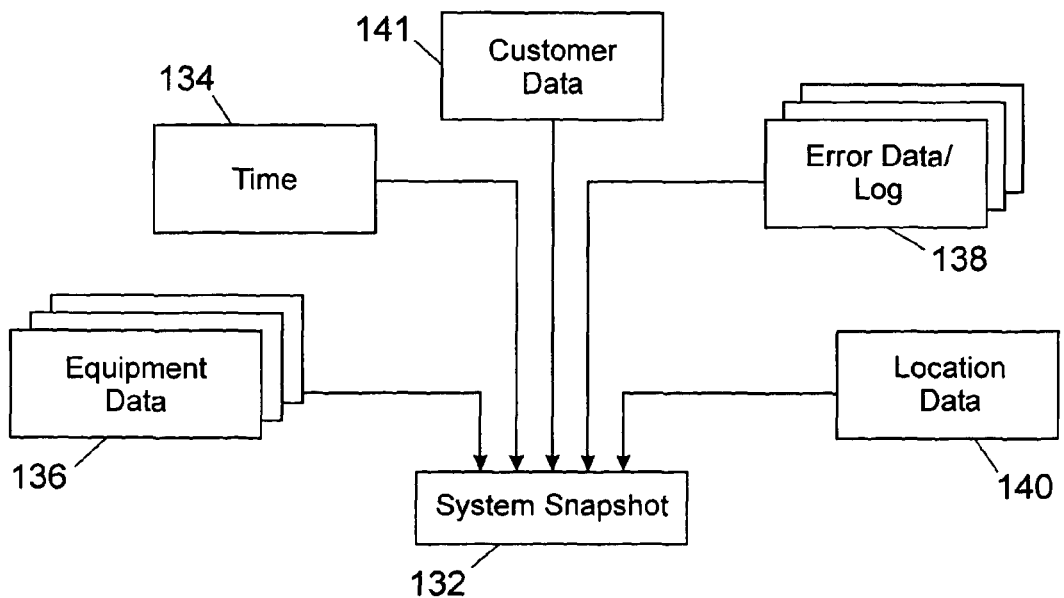
FIG. 7 is a diagrammatical representation of factors and components that may be included in a system snapshot in accordance with aspects of the present technique.

A particularly useful aspect of the present technique involves the generation of a system snapshot. As noted above, the system snapshot may include a range of information relating to the status of the serviced system at the time of occurrence of a serviceable event or condition. When the indicator or indicators of the serviceable event or condition are detected, then, the system snapshot may be generated. As illustrated in FIG. 7, the system snapshot, designated generally by reference numeral 132, may include a range of information and data then present on the system. Most usefully, the system snapshot will be generated contemporaneously with or very shortly after the detection of the indicator of the serviceable condition or event.

It should be noted that the snapshot may comprise data that is actually collected before, at the actual time of, and after the detection of the indicator. In general, however, the snapshot will include data collected at a time, or time span or window that is determined based upon the time of detection of the indicator. Where the indicator suggests an earlier time of the occurrence or onset of a condition, for example, the snapshot may include data corresponding to the system configuration at that earlier time. Where development or trending of the condition is of interest, earlier and later data may be collected. It should also be noted that the collection of the snapshot, and the period of the data collected may be based upon parameters other than time, such as counts of usage, cycles, and so forth. For the present purposes, these too should be considered as based on the "time" of detection of the indicator or occurrence of the indicator.

The system snapshot may include, for example, the term of the occurrence or detection of the indicator, certain equipment data, any log data and error data, location data and customer data, as indicated by reference numerals 134, 136, 138, 140, and 141, respectively. The time data will typically include indication of the date, hour and minute, or even the second at which the indicator was detected. Equipment data 136 may include software configuration information, historical parameters, images and other files present on the system, as well as a range of parameters and their values then present on the system.

Of particular interest in the present embodiment are hardware and software configuration information. Such hardware configuration information may include, for example, components installed and operative in the system, peripherals installed and operative in the system, parts, settings, connections established at the time of the occurrence, and so forth. The error data and log information 138 may include, for example, error names, error frequencies, monitored parameters outside of expected or tolerance ranges, and so forth. The location information 140—may include information such as the system, the subsystem, or even a component or field replaceable unit on which from which an indicator originated, as well as identification of the system, system location, customer, and so forth. The customer data 141 may include information such information as the customer and system numbers or designations, information relating to the customer or conditions of the sale or supply, and so forth.

Figure 8:
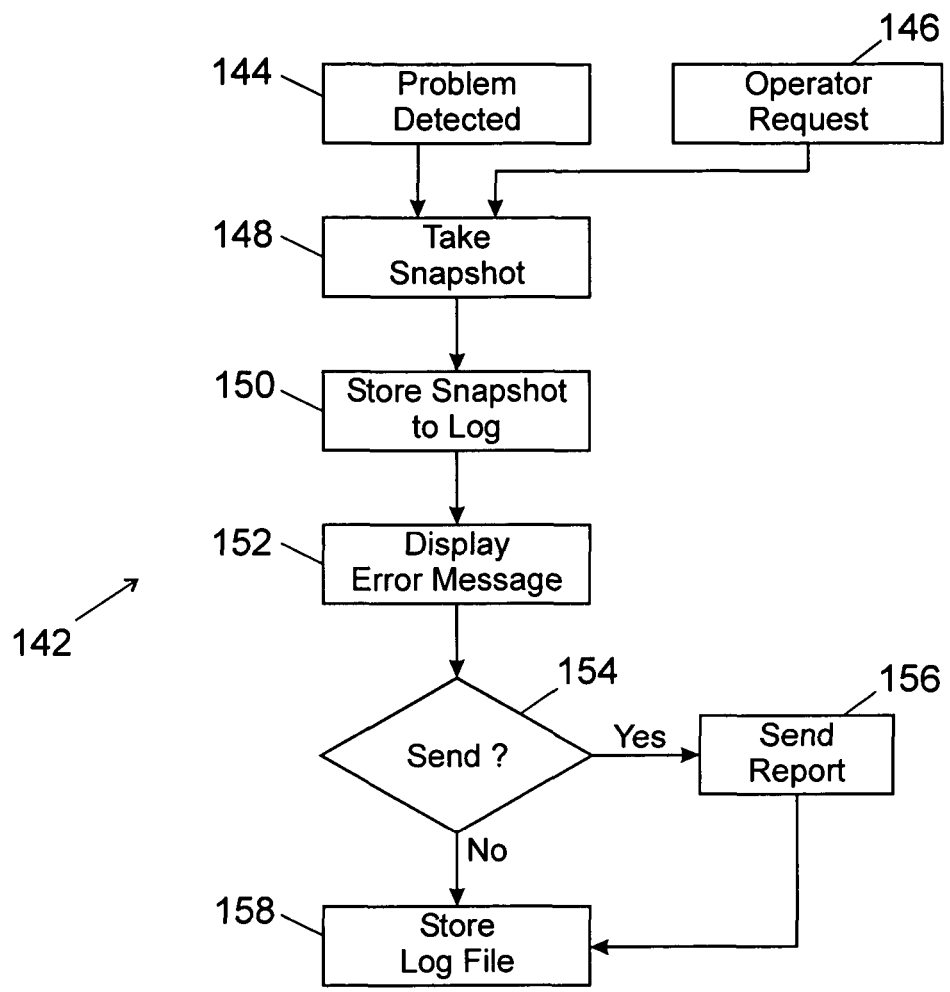
FIG. 8 is a flow chart illustrating exemplary processing used to capture the system snapshot for consideration with a service request or recommendation for service in response to such a request.

FIG. 8 represents exemplary steps in creating the system snapshot. The snapshot creation logic, designated generally by reference numeral 142, may begin with the detection of a problem as indicated at block 144. In fact, the system snapshot may be taken upon the detection of any indicator of interest, particularly those indicators which can be used for identifying a root cause of a problem, identifying a possible serviceable event or condition, or identifying possible responses to the event. Moreover, the snapshot may be taken upon the detection of any indicator which can be used to help prioritize serviceable events and conditions or responses to them. As indicated at reference numeral 146, moreover, such snapshots may be taken upon a request, such as from an operator. It should be noted that the operator may be local to the serviced system, or may be remote from the system. Thus, system snapshot may be initiated upon manual intervention, such as when an anomaly condition is suspected in a system. This may be in response to a local request or to a request from a remote service provider or any other operator.

At step 148 the system snapshot is taken. As noted above with reference to FIG. 7, the system snapshot will be taken by accessing certain files and data, and the snapshot will be stored in a log file indicated at step 150. The particular items to be stored in the system snapshot may be defined and stored within the serviced system. As will be appreciated by those skilled in the art, such information and instructions for initiating the system snapshot, may be defined in the ISKB, and downloaded to the system to define instructions needed for its creation. The instructions may also include certain processing to be performed on the collected data or files.

At step 152 in FIG. 8, an error message indicating that the indicator of a potentially serviceable event or condition has been detected may be displayed, where appropriate. Such displays of error messages are particularly desirable on systems in which a human operator may take some sort of action. In the medical diagnostics context, for example, complex systems may be controlled by clinicians, technicians, radiologists, and other professionals. The display of the error message at step 152 informs the operator that the system snapshot has been taken, and that some action may be warranted, such as initiating or transmitting a service request.

At step 154 the operator may be prompted to send the snapshot or a service request, or both, to a service provider for addressing the potentially serviceable condition or event. Based upon an operator selection, then, a report may be sent as indicated at reference numeral 156. In a present embodiment, whether the report is sent or not, the system snapshot is stored in a log file 158. Because certain events may not present an immediate impediment to continued operation or even normal operation of the system, the automatic storing of the system snapshot in a log file as indicated at step 158 may greatly facilitate later evaluation of the system health, servicing of the system, and so forth. The files may be accessed, for example, by service personnel or even remotely during routine check-ups or servicing of the system.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for operationally servicing medical diagnostic systems comprising:
   detecting an indicator of a serviceable condition in a serviced medical diagnostic system;
   automatically storing in the serviced medical diagnostic system snapshot data representative of a system configuration of the serviced medical diagnostic system upon detection of the indicator, wherein the system configuration comprises hardware configuration data and software configuration data for the serviced medical diagnostic system;
   automatically generating a request for service of the serviceable condition in the serviced medical diagnostic system;
   transmitting the service request and the snapshot data to a service provider;
   accessing a knowledge base including system data defining operational performance parameters of a plurality of serviced medical diagnostic systems, service data defining known serviceable conditions for the serviced medical diagnostic systems and potential indicators of the condition based upon the performance parameters, and response data defining a plurality of responses to the serviceable conditions;
   analyzing the snapshot data, wherein analyzing the snapshot data includes identifying associations between the snapshot data and the system data, service data, and response data accessed from the knowledge base;
   prioritizing a plurality of possible responses to the service request based upon the snapshot data and the response data, wherein the prioritization is adjusted based upon service contract data of the service data; and
   automatically generating a response to the service request based upon the prioritization of possible responses, wherein the response includes an indication of the priority of the response.

2. A method for operationally servicing medical diagnostic systems comprising:
   detecting an indicator of a serviceable condition in a serviced medical diagnostic system;
   automatically storing in the serviced medical diagnostic system snapshot data representative of a system configuration of the serviced medical diagnostic system upon detection of the indicator, wherein the system configuration includes data indicative of system components installed in the serviced medical diagnostic system and peripherals coupled to the serviced medical diagnostic system upon detection of the indicator, and wherein the system configuration comprises hardware configuration data and software configuration data for the serviced medical diagnostic system, the system components installed in the serviced medical diagnostic system, and the peripherals coupled to the serviced medical diagnostic system;

accessing a knowledge base including system data defining operational performance parameters of a plurality of serviced medical diagnostic systems, service data defining known serviceable conditions for the serviced medical diagnostic systems and potential indicators of the condition based upon the performance parameters, and response data defining a plurality of responses to the serviceable conditions;

analyzing the snapshot data, wherein analyzing the snapshot data includes identifying associations between the snapshot data and the system data, service data, and response data accessed from the knowledge base;

prioritizing a plurality of possible responses based upon the snapshot data and the response data, wherein the prioritization is adjusted based upon service contract data of the service data; and automatically generating a response based upon the prioritization of possible responses.

3. The method of claim 2, wherein the snapshot data includes data collected at a desired time based upon a time of detection of the indicator.

4. The method of claim 2, wherein the snapshot data includes data representative of an error present in the serviced medical diagnostic system upon detection of the indicator.

5. The method of claim 2, wherein system configuration includes at least one of software, hardware, firmware, network, location, and customer data.

6. The method of claim 2, further comprising automatically generating a request for service of the serviceable condition in the serviced medical diagnostic system, and transmitting the service request and the snapshot data to a service provider.

7. A method for operationally servicing medical diagnostic systems comprising:

detecting an indicator of a serviceable condition in a serviced medical diagnostic system;

automatically storing in the serviced medical diagnostic system snapshot data representative of a system configuration of the serviced medical diagnostic system upon detection of the indicator, wherein the system configuration includes data indicative of system components installed in the serviced medical diagnostic system and peripherals coupled to the serviced medical diagnostic system upon detection of the indicator, and wherein the system configuration comprises hardware configuration data and software configuration data for the serviced medical diagnostic system, the system components installed in the serviced medical diagnostic system, and the peripherals coupled to the serviced medical diagnostic system;

automatically generating a request for service of the serviceable condition in the serviced medical diagnostic system;

transmitting the service request and the snapshot data to a service provider, wherein the service request includes an indication of a priority of the service request;

accessing a knowledge base including system data defining operational performance parameters of a plurality of serviced medical diagnostic systems, service data defining known serviceable conditions for the serviced medical diagnostic systems and potential indicators of the condition based upon the performance parameters, and response data defining a plurality of responses to the serviceable conditions;

analyzing the snapshot data, wherein analyzing the snapshot data includes identifying associations between the snapshot data and the system data, service data, and response data accessed from the knowledge base; and automatically generating a response to the service request based upon the snapshot data and the response data.

8. The method of claim 7, wherein the snapshot data includes data collected at a desired time based upon a time of detection of the indicator.

9. The method of claim 7, wherein the snapshot data includes data representative of an error present in the serviced medical diagnostic system upon detection of the indicator.

10. The method of claim 7, wherein system configuration includes at least one of hardware, firmware, network, location, and customer data.

11. A method for operationally servicing medical diagnostic systems comprising:

receiving a request for service of a serviceable condition in a serviced medical diagnostic system, the request including snapshot data representative of a system configuration of the serviced medical diagnostic system upon detection of an indicator of the serviceable condition, wherein the system configuration includes data indicative of system components installed in the serviced medical diagnostic system and peripherals coupled to the serviced medical diagnostic system upon detection of the indicator, and wherein the system configuration comprises hardware configuration data and software configuration data for the serviced medical diagnostic system, the system components installed in the serviced medical diagnostic system, and the peripherals coupled to the serviced medical diagnostic system;

accessing a knowledge base stored in a computer-readable storage device, wherein the knowledge base includes system data defining operational performance parameters of a plurality of serviced medical diagnostic systems, service data defining known serviceable conditions for the serviced medical diagnostic systems and indicators of potential malfunction based upon the performance parameters, and response data defining a plurality of responses to the serviceable conditions;

analyzing the snapshot data, wherein analyzing the snapshot data includes identifying associations between the snapshot data and the system data, service data, and response data accessed from the knowledge base;

prioritizing a plurality of possible responses based upon the snapshot data and the response data, wherein the prioritization is adjusted based upon service contract data of the service data; and automatically generating a response to the service request based upon the prioritization of possible responses, wherein the response includes an indication of the priority of the response.

12. The method of claim 11, wherein the snapshot data includes data representative of a time of detection of the indicator.

13. The method of claim 11, wherein the snapshot data includes data representative of an error present in the serviced medical diagnostic system upon detection of the indicator.

14. The method of claim 11, wherein system configuration includes at least one of software, hardware, firmware, network, location, and customer data.

15. A device including a non-transitory computer storage medium having executable computer code encoded thereon, the computer code including:

code for detecting an indicator of a serviceable condition in a serviced medical diagnostic system, code for automatically storing in the serviced medical diagnostic system snapshot data representative of a system configuration of the serviced medical diagnostic system upon detection of the indicator, wherein the system configuration comprises hardware configuration data and software configuration data for the serviced medical diagnostic system, code for automatically generating a request for service of the serviceable condition in the serviced medical diagnostic system, code for transmitting the service request and the snapshot data to a service provider, code for accessing a knowledge base including system data defining operational performance parameters of a plurality of serviced medical diagnostic systems, service data defining known serviceable conditions for the serviced medical diagnostic systems and potential indicators of the condition based upon the performance parameters, and response data defining a plurality of responses to the serviceable conditions, code for analyzing the snapshot data, wherein analyzing the snapshot data includes identifying associations between the snapshot data and the system data, service data, and response data accessed from the knowledge base, code for prioritizing a plurality of possible responses to the service request based upon the snapshot data and the response data, wherein the prioritization is adjusted based upon service contract data of the service data, and code for automatically generating a response to the service request based upon the prioritization of possible responses, wherein the response includes an indication of the priority of the response.

16. A device including a non-transitory computer storage medium having executable computer code encoded thereon, the computer code including:
code for detecting an indicator of a serviceable condition in a serviced medical diagnostic system, code for automatically storing in the serviced medical diagnostic system snapshot data representative of a system configuration of the serviced medical diagnostic system upon detection of the indicator, wherein the system configuration includes data indicative of system components installed in the serviced medical diagnostic system and peripherals coupled to the serviced medical diagnostic system upon detection of the indicator, and wherein the system configuration comprises hardware configuration data and software configuration data for the serviced medical diagnostic system, the system components installed in the serviced medical diagnostic system, and the peripherals coupled to the serviced medical diagnostic system, code for accessing a knowledge base including system data defining operational performance parameters of a plurality of serviced medical diagnostic systems, service data defining known serviceable conditions for the serviced medical diagnostic systems and potential indicators of the condition based upon the performance parameters, and response data defining a plurality of responses to the serviceable conditions, code for analyzing the snapshot data, wherein analyzing the snapshot data includes identifying associations between the snapshot data and the system data, service data, and response data accessed from the knowledge base, code for prioritizing a plurality of possible responses based upon the snapshot data and the response data, wherein the prioritization is adjusted based upon service contract data of the service data, and code for automatically generating a response based upon the prioritization of possible responses.

17. A device including a non-transitory computer storage medium having executable computer code encoded thereon, the computer code including:
code for receiving a request for service of a serviceable condition in a serviced medical diagnostic system, the request including snapshot data representative of a system configuration of the serviced medical diagnostic system upon detection of an indicator of the serviceable condition, wherein the system configuration includes data indicative of system components installed in the serviced medical diagnostic system and peripherals coupled to the serviced medical diagnostic system upon detection of the indicator, and wherein the system configuration comprises hardware configuration data and software configuration data for the serviced medical diagnostic system, the system components installed in the serviced medical diagnostic system, and the peripherals coupled to the serviced medical diagnostic system, wherein the service request includes an indication of a priority of the service request, code for accessing a knowledge base including system data defining operational performance parameters of a plurality of serviced medical diagnostic systems, service data defining known serviceable conditions for the serviced medical diagnostic systems and indicators of potential malfunction based upon the performance parameters, and response data defining a plurality of responses to the serviceable conditions, code for analyzing the snapshot data, wherein analyzing the snapshot data includes identifying associations between the snapshot data and the system data, service data, and response data accessed from the knowledge base, and code for automatically generating a response to the service request based upon the snapshot data and the response data.

* * * * *